US009064040B2

(12) United States Patent
Sudharsan (10) Patent No.: US 9,064,040 B2
(45) Date of Patent: Jun. 23, 2015

(54) ADAPTIVE ANALYTICAL BEHAVIORAL AND HEALTH ASSISTANT SYSTEM AND RELATED METHOD OF USE

(71) Applicant: WellDoc, Inc., Baltimore, MD (US)

(72) Inventor: Bharath Sudharsan, Baltimore, MD (US)

(73) Assignee: WellDoc, Inc., Baltimore, MD (US)

( * ) Notice: Subject to any disclaimer, the term of this patent is extended or adjusted under 35 U.S.C. 154(b) by 0 days.

(21) Appl. No.: 14/462,033

(22) Filed: Aug. 18, 2014

(65) Prior Publication Data

US 2014/0358581 A1    Dec. 4, 2014

Related U.S. Application Data

(63) Continuation of application No. 13/428,763, filed on Mar. 23, 2012, now Pat. No. 8,838,513.

(60) Provisional application No. 61/467,131, filed on Mar. 24, 2011.

(51) Int. Cl.
*G06N 5/00* (2006.01)
*G06Q 10/00* (2012.01)
*G06F 19/00* (2011.01)
*G06N 7/00* (2006.01)

(52) U.S. Cl.
CPC .............. *G06F 19/345* (2013.01); *G06N 7/005* (2013.01)

(58) Field of Classification Search
None
See application file for complete search history.

(56) References Cited

U.S. PATENT DOCUMENTS

| | | | |
|---|---|---|---|
| 5,769,074 A | 6/1998 | Barnhill et al. |
| 7,447,643 B1 | 11/2008 | Olson et al. |
| 7,769,600 B2 | 8/2010 | Iliff |
| 8,034,558 B2 | 10/2011 | Smith et al. |
| 8,036,915 B2 | 10/2011 | Kremer et al. |
| 8,140,270 B2 | 3/2012 | Kingsmore et al. |
| 2002/0026103 A1 | 2/2002 | Norris et al. |
| 2004/0199482 A1 | 10/2004 | Wilson |
| 2005/0086082 A1 | 4/2005 | Braunstein et al. |
| 2008/0228043 A1 | 9/2008 | Kenedy et al. |
| 2009/0030290 A1 | 1/2009 | Kozuch et al. |

(Continued)

FOREIGN PATENT DOCUMENTS

WO WO 2007/143083 A2 12/2007
WO WO 2008/103827 A1 8/2008

OTHER PUBLICATIONS

Riley, William T et al., "Health Behavior Models in the Age of Mobil Interventions: Are Our Theories up to the Task?" *TBM*, pp. 53-71.

(Continued)

*Primary Examiner* — Alan Chen
(74) *Attorney, Agent, or Firm* — Bookoff McAndrews, PLLC (57) ABSTRACT

This present disclosure relates to systems and methods for providing an Adaptive Analytical Behavioral and Health Assistant. These systems and methods may include collecting one or more of patient behavior information, clinical information, or personal information; learning one or more patterns that cause an event based on the collected information and one or more pattern recognition algorithms; identifying one or more interventions to prevent the event from occurring or to facilitate the event based on the learned patterns; preparing a plan based on the collected information and the identified interventions; and/or presenting the plan to a user or executing the plan.

30 Claims, 3 Drawing Sheets (56) References Cited

U.S. PATENT DOCUMENTS

2010/0324936 A1   12/2010   Vishnubhatla et al.
2012/0123234 A1*  5/2012   Atlas et al. .................... 600/365

OTHER PUBLICATIONS

Lustria, Mia Liza et al., "Computer-Tailored Health Interventions Delivered Over the Web: Review and Analysis of Key Components," *Elsevier-Patent Education and Counseling*, 74, pp. 156-173 (2009).
Healthways—The Solution for Well-Being Improvement, www.Healthways.com/PositiveChange (6 pgs.).
International Search Report and Written Opinion issued in counterpart International Application No. PCT/US2012/030367 (8 pgs.).

* cited by examiner

ADAPTIVE ANALYTICAL BEHAVIORAL AND HEALTH ASSISTANT SYSTEM AND RELATED METHOD OF USE

CROSS REFERENCE TO RELATED APPLICATIONS

This application is a continuation of pending U.S. application Ser. No. 13/428,763, filed on Mar. 23, 2012, which claims the benefit under 35 USC §119 and 120 to U.S. Provisional Application No. 61/467,131, filed on Mar. 24, 2011, the entireties of which are incorporated herein by reference.

FIELD OF THE DISCLOSURE

Embodiments of the present disclosure relate to systems and methods that aid in a decision-making process. In particular, exemplary embodiments of the present disclosure relate to aiding a decision-making process for health or medical purposes.

BACKGROUND OF THE DISCLOSURE

The management of digital healthcare information is important. Attempts have been made to provide diagnosis, medical decision support, and healthcare information management using individual data. These systems, however, lack the ability to empower patients to self-manage post-diagnosis care. For example, these prior attempts fail to use the individual data to provide advice in order to achieve one or more clinical goals.

One problem with prior attempts is that they lack the ability to make analytical inferences from a patient's behavior and/or clinical data. For example, they lack the ability to adapt an action plan based on discovering one or more patterns associated with the patient. Moreover, the prior attempts are not "smart," because they lack the ability to learn. The systems and methods described herein solve one or more of these problems, or other problems with the prior attempts.

SUMMARY

The present disclosure includes many embodiments. For example, in an embodiment, systems and methods for providing an Adaptive Analytical Behavioral and Health Assistant (AABHA) are disclosed.

An aspect of the present disclosure may include a computer-implemented method for providing a health assistant system for dynamically creating a plan. The method may include collecting one or more of patient behavior information, clinical information, or personal information. The method may further include learning one or more patterns that cause an event based on the collected information and one or more pattern recognition algorithms. The method may further include identifying one or more interventions to prevent the event from occurring or to facilitate the event based on the learned patterns. The method may further include preparing the plan based on the collected information and the identified interventions. The method may further include presenting the plan to a user or executing the plan.

Various embodiments of the disclosure may include one or more of the following aspects: receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

A further aspect of the present disclosure may include an information processing device for determining a plan. The device may include a processor for processing a set of instructions. The device may also include a computer-readable storage medium for storing the set of instructions, wherein the instructions, when executed by the processor, perform a method. The method may include collecting one or more of patient behavior information, clinical information, or personal information. The method may further include learning one or more patterns that cause an event based on the collected information and a pattern recognition algorithm. The method may further include identifying one or more interventions to prevent the event from occurring based on the learned patterns. The method may further include preparing the plan based on the collected information and the identified interventions. The method may further include presenting the plan to a user.

Various embodiments of the disclosure may include one or more of the following aspects: receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

Another aspect of the present disclosure includes a non-transitory computer-readable medium storing a set of instructions that, when executed by a processor, perform a method for determining an plan. The method may include collecting one or more of patient behavior information, clinical information, or personal information. The method may further include learning one or more patterns that cause an event based on the collected information and a pattern recognition algorithm. The method may further include identifying one or more interventions to prevent the event from occurring based on the learned patterns. The method may further include preparing the plan based on the collected information and the identified interventions. The method may further include presenting the plan to a user.

Various embodiments of the disclosure may include one or more of the following aspects: receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

DESCRIPTION OF THE EMBODIMENTS

Figure 1:
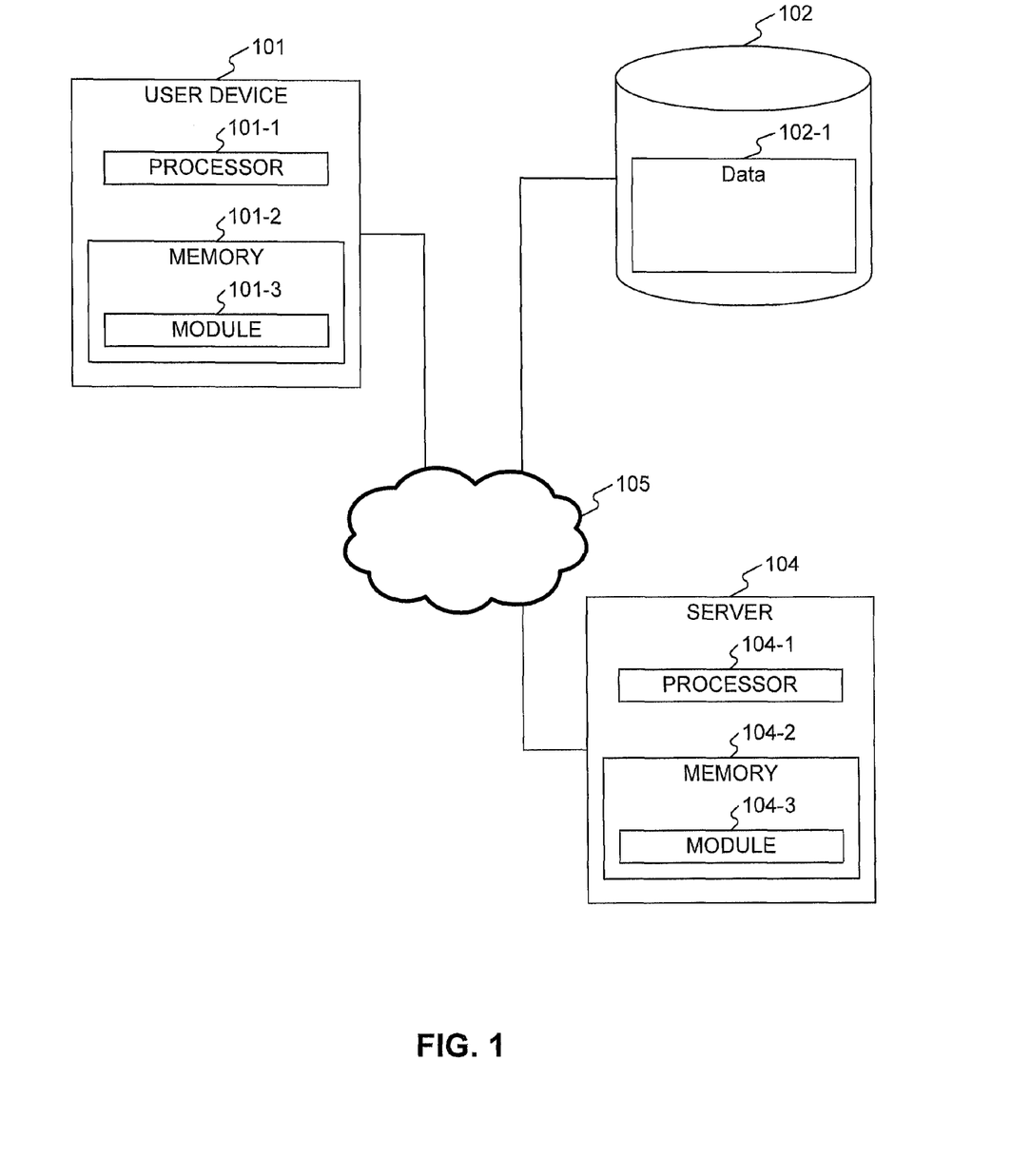
FIG. 1 depicts a system for providing a health assistant consistent with an embodiment of the current disclosure.

FIG. 1 depicts an embodiment 100 that may use one or more devices, such as user device 101 and server 104, to aid in a decision making process. The decision making process may include processes that manage a patient's health or medical fitness, manage finances, or manage device maintenance and/or repair. For example, these processes may include one or more of the following: 1) determining whether to change a diet, 2) determining whether to order more medication, 3) determining whether to contact a doctor, 4) determining whether to change an exercise routine, or 5) determining whether to rest. As a result, a plan for a particular patient may be developed. These processes may, additionally or alternatively, include one or more of the following: 1) determining whether to buy or sell an asset, 2) determining whether to conduct maintenance, 3) determining whether to order or replace a part, or 4) determining whether to take a product out of service.

User device 101 and server 104 may be any type of general computing device, such as a mobile computing device, laptop, netbook, server, cell phone, smart phone, personal digital assistant, tablet computer, or any other device capable of executing one or more instructions. User device 101 and server 104 may contain one or more processors, such as processors 101-1 and 104-1. Processors 101-1 and 104-1 may be a central processing unit, a microprocessor, a general purpose processor, an application specific processor, or any device that executes instructions. User device 101 and server 104 may also include one or more memories, such as memory 101-2 and 104-2, that store one or more software modules. Memory 101-2 and 104-2 may be implemented using any computer-readable storage medium, such as hard drives, CDs, DVDs, flash memory, RAM, ROM, etc. Memory 101-2 may store a module 101-3, which may be executed by processor 101-1. Similarly, memory 104-2 may store a module 104-3, which may be executed by processor 104-1.

Modules 101-3 and 104-3 may provide one or more services or engines, such as an Adaptive Pattern Service ("APS"), a Statistical Service ("SS"), a Cause-Effect Modeling Service ("CEMS") or just Modeling Service ("MS"), an Intervention Logistics Service ("ILS"), a Delivery Service ("DS"), a Clinical Analysis Service ("CAS"), or any other service or engine. A combination of these services or engines may operate to provide an Adaptive Analytical Behavioral and Health Assistant in accordance with embodiments of the present disclosure. In one embodiment, as a use case, a patient may be a 40 year old Asian male with diabetes that has inadequate blood glucose control.

User device 101 may further comprise one or more user interfaces (not shown). The user interface may include one or more of a screen, a display, a projector, a touch panel, a pointing device, a scrolling device, a button, a switch, a motion sensor, an audio sensor, a pressure sensor, a thermal sensor, etc. The user interface may allow one or more interfaces to present information to a user, such as a plan or intervention. The user interface may be web based, such as a web page, or a stand-alone application. The user interface may also be configured to accept information about a user, such as user feedback. The user may manually enter the information, or it may be entered automatically. In the use case, the patient (or the patient's caretaker) may enter information such as when medication was taken or what the patient consumed. For example, user device 101 may include testing equipment (not shown) or an interface for receiving information from testing equipment. Testing equipment may include, for example, a blood glucose meter or heart rate monitor. The user device 101 may also include one or more sensors (not shown), such as a camera or microphone, for collecting feedback from a user. In the use case, the device may include a glucose meter for reading and automatically reporting the patient's blood glucose levels.

The system 100 may also include one or more databases, such as database 102. While FIG. 1 depicts database 102 as a separate device, database 102 may alternatively be located in user device 101 and/or server 104. Database 102 may be implemented using any database technology known to one of ordinary skill in the art, such as relational database technology or object-oriented database technology.

Database 102 may store data 102-1. Data 102-1 may include 1) a knowledge base for making inferences, 2) statistical models, and/or 3) patient information. Data 102-1, or portions thereof, may be alternatively or simultaneously stored in server 104 or user device 101.

System 100 also may include a network 105 for facilitating communications between user device 101, server 104, and/or database 102. The network 105 may include wireless or wired links, such as mobile telephone networks, Wi-Fi, LANs, WANs, Bluetooth, near-field communication (NFC), etc.

Figure 2:
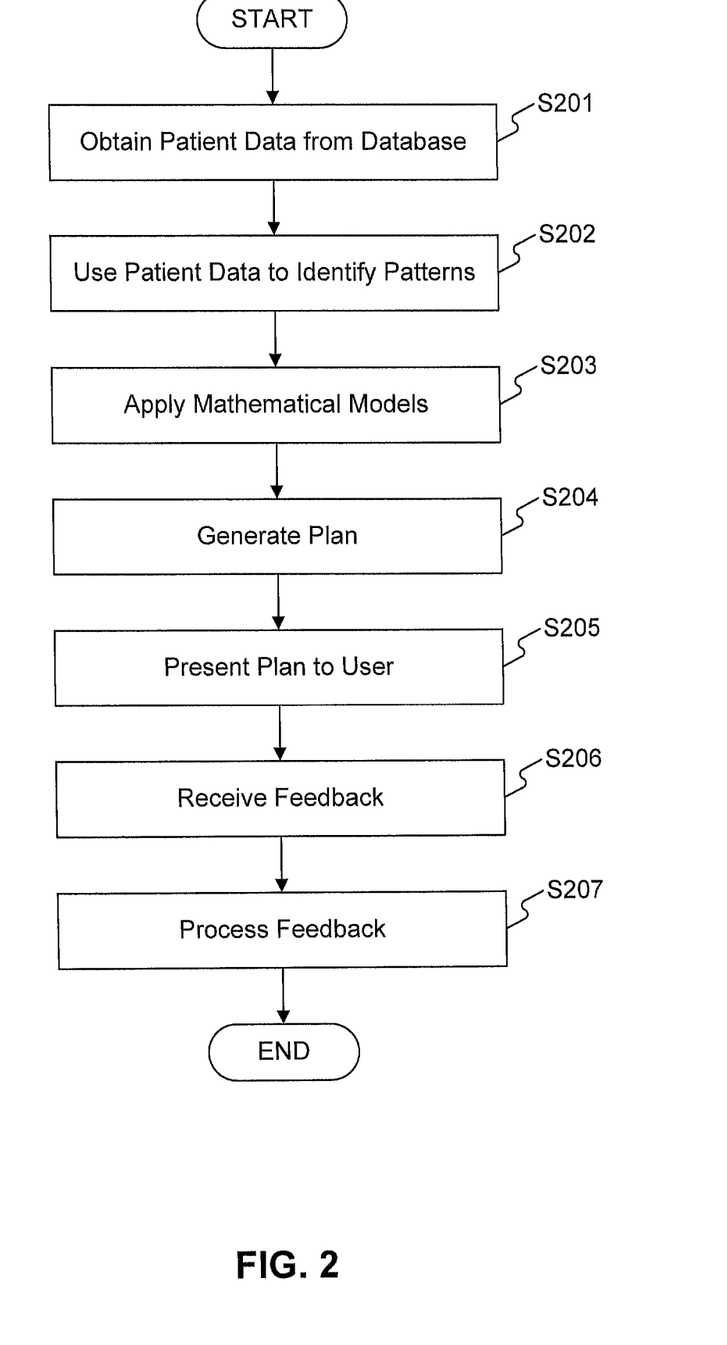
FIG. 2 depicts a flowchart preparing a plan for a user consistent with an embodiment of the current disclosure.

FIG. 2 depicts a process for providing an Adaptive Analytical Behavioral and Health Assistant, in accordance with one embodiment of the present disclosure. In step S201, user device 101 or server 104 may obtain data for one or more patients from database 102. Then, in step S202, user device 101 and/or server 104 may use the patient data to identify one or more patterns. This may be achieved, for example, by an APS.

Next, in step S203, user device 101 or server 104 may apply one or more mathematical models (e.g., the mathematical models discussed below) to the data. The application of the models may provide insight into the dynamics of a patient's behavior or possible causes of an observed behavior. The models may be applied or supplied by a GEMS or MS.

User device 101 or server 104 may then use the results of the application to develop one or more plans for a patient or user (S204). The development of the plan may be performed, for example, by an Intervention Logistics Service ("ILS"). The user interface may then present the plan to the patient or user (S205) or execute the plan, using, for example, the DS. User device 101 may then receive feedback from the patient or user, testing equipment, or other sensory data (S206) and either process the feedback itself, or send the feedback to the server 104 for processing by one or more of the services or engines.

While steps S201-S207 are depicted in a particular order, the principles of the present disclosure are not limited to the order depicted in FIG. 2. Additionally, embodiments of the process can include more or less steps than those depicted in FIG. 2.

Figure 3:
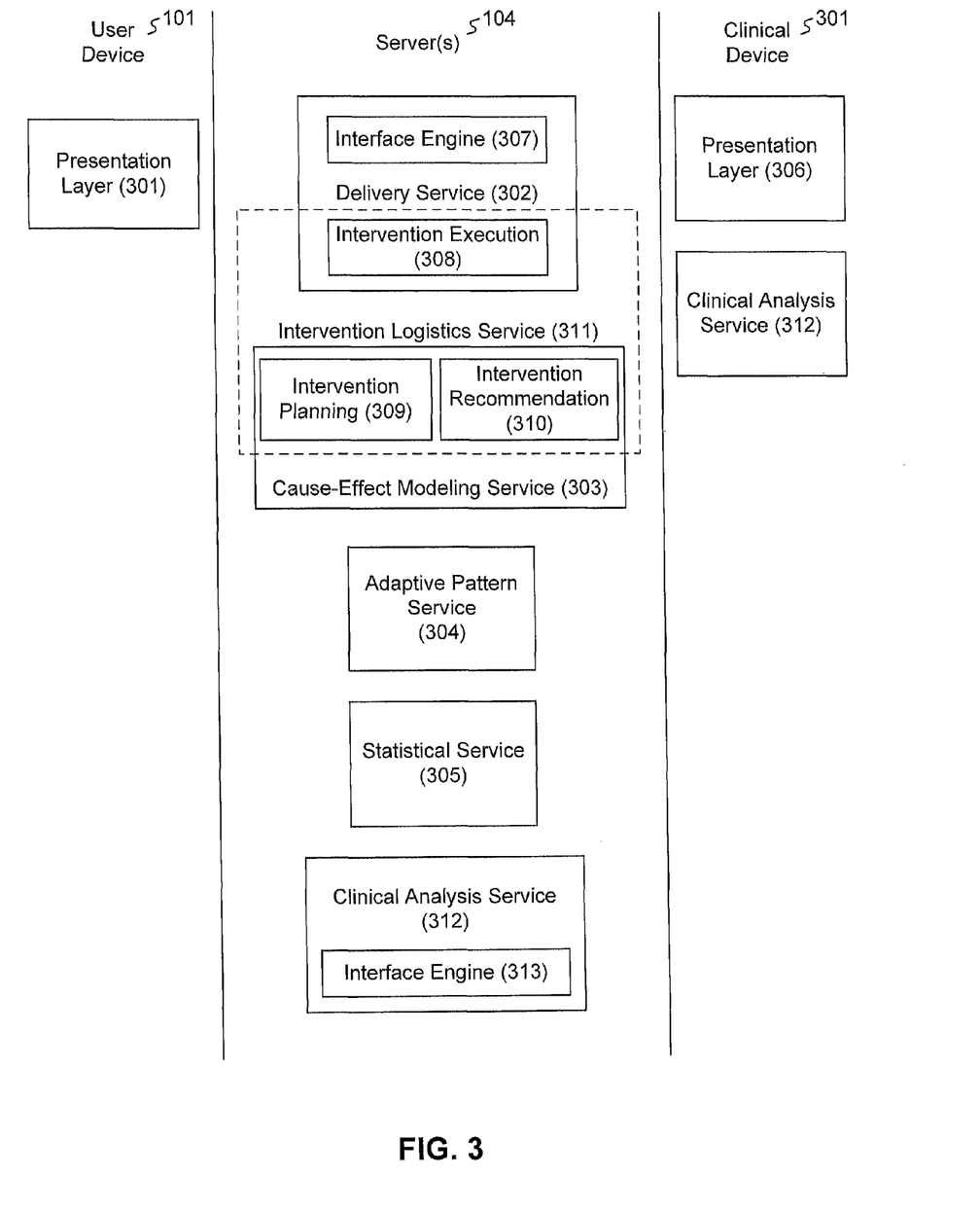
FIG. 3 depicts a system for providing a health assistant consistent with an embodiment of the current disclosure.

FIG. 3 displays an exemplary embodiment including user device 101, server 104, and a clinical device 301. User device 101 may include a presentation layer 301. Presentation layer 301 may be a web browser, application, messaging interface (e.g., e-mail, instant message, SMS, etc.), etc. The user device 101 may present an action plan, notifications, alerts, reading materials, references, guides, reminders, or suggestions to a user via presentation layer 301. For example, the presentation layer 301 may present articles that are determined to be relevant to the user, reminders to purchase medications, tutorials on topics (e.g., a tutorial on carbohydrates), testimonials for others with symptoms, and/or one or more goals (e.g., a carbohydrate counting goal). The presentation layer 301 may also present information such as a tutorial (e.g., a user guide or instructional video) and/or enable communications between the healthcare provider and the user. The communications between the healthcare provider and the user may be via electronic messaging (e.g., e-mail or SMS), voice, or real-time video. One or more of these items may be presented based on the action plan (e.g., as an intervention) or a determination by one or more of APS 304, SS 305, CEMS 303, ILS 311, DS 302, CAS 312, etc. Presentation layer 301 may also be used to receive feedback from a user, as discussed above. This may include, for example, monitoring a patient's actions, a user's attitude, or a user's belief. Server 104 may include one or more of APS 304, SS 305, GEMS 303, ILS 311, DS 302, CAS 312, etc.

Clinical device 301 may include a presentation layer 306 and/or CAS 312. While a single clinical device 301 is shown, the system may include multiple clinical devices. For example, one or more of a patient's physician, therapist, health insurance, or nurse may have a clinical device 301. Presentation layer 306 or CAS 312 may be used to provide reminders, notifications, etc. similar to those presented to the user above. For example, the system may send a notification to a healthcare provider to open a report on a patient's observed medication patterns. This notification may be sent, for example, in response to a determination that the patient has a tendency to manage symptoms (e.g., low blood sugar) with medication alone and/or runs out of medication early. A notification may also be sent to the healthcare provider to discuss one or more topics with a patient. For example, when a client has a pattern of managing low blood sugar with medication alone and then overeats, causing worse symptoms, the system my notify the healthcare provider to discuss, e.g., the relationships between carbohydrates and the medication with the patient. Presentation layer 306 or CAS 312 may also be used to communicate with a user or patient, as discussed above.

Clinical Device 301 may also be used by a clinical analyst. The clinical analyst may use presentation layer 306 or CAS 312 to design metrics, prepare data, set thresholds, design models, define rules, and/or manage knowledge.

DS 302 may include an interface engine 307 and/or intervention execution engine 308. Interface engine 307 may be, for example, a web server that provides a webpage or portal to presentation layer 301 and/or presentation layer 306. Alternatively, interface engine 307 may comprise an application program interface (API) that provides an interface to presentation layer 301, presentation layer 306, and/or CAS 313. The interface engine 307 may, for example, provide one or more notifications to presentation layer 301 and/or presentation layer 306. Intervention execution engine 308 may provide a means for executing interventions included in an action plan. Intervention execution engine 308 may facilitate notifications, tutorials, reminders, and/or communication with a healthcare provider, etc. when needed to lower the probability that an event will occur.

In a use case, a patient, Srini, may be 47 years old with diabetes and heart problems. Without assistance, Srini may experience heart pain and run out of medication and need to go to the emergency room. The system may detect that Srini was feeling low (e.g., his blood glucose was low) and he managed this with medication alone. Then, he compensated with too much food. This caused the symptoms to worsen, which led to more medication only management. This led to running out of medication. Which led to low blood sugar again and more severe symptoms, including heart pain. To prevent this, the system may take the following actions:

a. In a first week, there may be an article on the importance of dosage, a reminder may be issued to a patient and/or caregiver about medication purchase for the month, and/or a notification to a heath care provider to open report on observed medication patterns.

b. In week two, there may be a notification sent to a patient to view a tutorial on carbohydrates, a notification to the health care provider to specifically talk to the patient about the relationship between carbohydrates and medication, a testimonial of those with shortness of breath, and a suggestion to the patient to set a carbohydrate counting goal.

These interventions may limit the probability of having severe symptoms and prevent the patient from needing to go to the hospital.

CEMS 303 may include an intervention planning engine 309 and/or an intervention recommendation engine 310. Intervention planning engine 309 and/or intervention recommendation engine 310 may define the criteria or trigger for notifications, tutorials, reminders, and/or communication with a healthcare provider, etc. when needed to lower the probability that an event will occur. Intervention planning engine 309 and/or intervention recommendation engine 310 may use intervention execution engine 308 to facilitate these functions.

CAS 312 may be located in server 104 and/or clinical device 301. CAS 312 may include an interface engine 313. Interface engine 313 may be a web server that presents a webpage for performing clinical analysis to presentation layer 306. Interface engine 313 may also be an API for communication with CAS 312 or clinical device 301.

ILS 311 may include intervention execution engine 308, intervention planning engine 309, and/or intervention recommendation engine 310. One or more of these engines may also be part of DS 302 and/or CEMS 303.

The APS 304 may act as an agent for identifying one or more patterns from data, and may be implemented using some or all of the features of the APS 304 described below. The data may be, for example, behavioral, clinical, and/or personal in nature, and may be stored in one or more databases. This can include medical records, meter readings (e.g., blood glucose meter, heart monitor, etc.), data collected for user interactions (e.g., emails, Internet usage, blog or social media posts, mood determined by voice pattern or facial recognition, etc.), data entered by a user or an associated user (e.g., logs of food, exercise, symptoms, lifestyle, likes/dislikes, hobbies etc.), positional information (e.g., GPS information, information inferred based on mobile device usage, etc.), information about a patient's attitude and/or beliefs, perceptions, personality traits, cognitive abilities & skills, emotional intelligence, psychological traits, etc. These one or more databases may be part of server 104 or remotely located. The APS 304 may include support for continuous, ordinal, and/or nominal data types. The APS 304 may employ pattern recognition, relationship discovery, hierarchical inference, etc. The APS 304 may include knowledge-based components, training-based components, and/or inference-based components. In the use case, patterns may include one or more simple patterns (e.g., the patient has more carbohydrates in the second week of the month), patterns of patterns (e.g., the trend of eating more carbohydrates in the second week continues for two months), differing patterns (e.g., that patient stops testing in the first week of one month and in the third week of another month).

In one embodiment, the APS 304 may obtain a pattern definition in a simple format; predict several time steps in future by using Markov models; optimize results based on its predictions; detect transition between patterns; abstract data and extract information to infer higher levels of knowledge; combine higher and lower levels of information to understand about the patient and clinical behaviors; infer from multi-temporal (different time scales) data and associated information; using variable order Markov models, and/or reduce noise over time by employing clustering algorithms, such as k-means clustering.

For example, K vectors are randomly chosen and assigned as a cluster center for applying k-means clustering algorithms. In pattern recognition, the k-means is a method for classifying objects based on the closest training examples in the feature space. k-NN is a type of instance based learning, or lazy learning, where the function is only approximated locally and all computation is differed until classification. The Euclidian distance between different patterns in this vector space may be used to find clusters of patterns. The system may assign a new input vector to its closest cluster center and may move that cluster towards the input vector by a fraction of the Euclidean distance between them.

The APS may use knowledge-based components such as a knowledge-based repository (KB). The repository may include clinical information. For example, it may include that "eating carbohydrate-rich food causes blood glucose to increase." The information may be stored in a variety of formats based on the type of inference employing them. The knowledge-based repository may act as a repository for some or all of the referenced knowledge. For example, it can include reference values for certain consents and variables used for inference. Accordingly, one or more layers (e.g. a hierarchical pattern processing layer or Advanced Pattern Engine) may subscribe to information from the knowledge-based repository. For example, one or more of the services may query the knowledge-based repository when making an inference.

In one embodiment, the knowledge-based repository may aggregate relevant clinical and/or behavioral knowledge from one or more sources. In an embodiment, one or more clinical and/or behavioral experts may manually specify the required knowledge (e.g., using CAS 312). In another embodiment, an ontology-based approach may be used. For example, the knowledge-based repository may leverage the semantic web using techniques, such as statistical relational learning (SRL).

SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'Asian male' and 'smartness', they may be connected using the relationship 'asian males are smart'. This relationship may be given a weight (e.g., 0.3). This relationship may vary from time to time (populations trend over years/decades). By leveraging the knowledge in the semantic web (e.g., all references and discussions on the web where 'asian male' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpora of relevant objects and/or textual resources. These techniques may be used to not only to obtain first-order waited formulae for clinical parameters, but also general information. This information may then be used when making inferences.

For example, if the first order logic is 'obesity causes diabetes', there are two objects involved: obesity and diabetes. If data on patients with obesity and as to whether they were diagnosed with diabetes or not is available, then the weights for this relationship may be learnt from the data. This may be extended to non-clinical examples such as person's mood, beliefs etc.

The APS 304 may use the temporal dimension of data to learn representations. The APS 304 may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of an matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern i is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

In one embodiment, the probability of a transition between two patterns may be used as the similarity between those patterns for the HC algorithm. The similarity metric may be used to cluster medical patterns that are likely to follow one another into the same cluster. The HC algorithm may be configured such that patterns that are unlikely to follow each other fall into different clusters. A cluster of a set of patterns that are likely to follow each other in time may be referred to as a temporal group. The HC algorithm may start with all store patterns and separate clusters and then recursively merge clusters with the greatest similarity. This may be used to obtain a treelike structure (e.g. a dendrogram) with a single cluster (which may contain all patterns) at the top of the tree and the individual patterns at the bottom (e.g. each pattern in its own cluster). The system may achieve the desired clustering for temporal grouping (e.g. somewhere between the bottom and a top of the dendrogram) by defining a suitable criteria. For example, one criterion could be to cut the tree at a level where the size of the largest cluster does not exceed a particular value. The node may have a design perimeter that sets the maximum number of clusters or temporal groups of the node. The desired temporal groups may be achieved by selecting a level of the dendrogram that gives the number of temporal groups closest to and less than the configured maximum number of temporal groups. These temporal groups may be updated as the Markov transition probabilities are updated. These steps may be performed periodically during the learning process. The learning process may be stopped once the temporal groups have sufficiently stabilized.

Once a node has completed its learning process, it may be used for sensing and/or inference. The characteristics of the input to the node in sensing may be identical to those used during learning. For example, objects may move under the field of view of the node and the node may see portions of those objects. The resulting patterns may be used as inputs to the node.

A node used for sensing and/or inference may produce an output for every input pattern. A node may also use a sequence of patents to produce an output. In one embodiment, it can be assumed that the outputs are produced based on instantaneous inputs. Under this assumption, the Markov graph may not be used during the sensing phase. For example, it may be discarded once the temporal groups within the node are completed.

For every input pattern, the node may produce an output factor that indicates the degree of membership of the input pattern and each of its temporal groups. However, the current input pattern may not perfectly match any of the patterns stored in memory. Accordingly, in one embodiment, the closeness of the input pattern to every pattern stored in memory will be determined. For example, let $d_i$ be the distance of the $i^{th}$ stored pattern from the input pattern. The larger this distance is, the smaller the match between the input pattern and the stored pattern becomes. Assuming that the probability that an input pattern matches a stored pattern falls off as a Gaussian function of the Euclidean distance, the probability that the input pattern matches the $i^{th}$ stored pattern can be calculated as being proportional to $e^{-d2i/\alpha}$, where $\alpha$ is a parameter of the node. Calculating this for every stored pattern may give the closeness of the current input pattern to all the vertices of the Markov graph.

Degree of membership of the input pattern in each temporal group may be determined by the maximum of its closeness to each of the vertices within the temporal group. This results in a length equal to the number of temporal groups, with each component of the factor indicating the degree of membership of the input pattern in the corresponding temporal group. This factor may then be used normalize the sum to unity. These normalized memberships may be used as estimates of probability of membership in each temporal group. This normalized degree of membership may also be used as an output of the node. The output may be a histogram giving estimates of probability of membership of the current input pattern and each of the temporal groups of the node.

As data is fed into the APS 304, the transition probabilities for each pattern and pattern-of-patterns (POP™) may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The APS 304 may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the $(p+1)^{th}$ occurrence. Then, the process may be repeated. This may be done until the APS 304 predicts logical relationships up to a specified accuracy threshold. Then, the results may be considered optimal.

When a node is at the first level of the hierarchy, its input may come directly from the data source, or after some pre-processing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

The APS 203 may also be adaptive. In one embodiment, every level has a capability to obtain feedback information from higher levels. This feedback may inform about certain characteristics of information transmitted bottom-up through the network. Such a closed loop may be used to optimize each level's accuracy of inference as well as transmit more relevant information from the next instance.

The APS 203 may learn and correct its operational efficiency over time. This process is known as the maturity process of the system. The maturity process may include one or more of the following flow of steps:
  a. Tracking patterns of input data and identifying pre-defined patterns (e.g. if the same pattern was observed several times earlier, the pattern would have already taken certain paths in the hierarchical node structure).
  b. Scanning the possible data, other patterns, and POP™ (collectively called Input Sets (IS)) required for those paths. It also may check for any feedback that has come from higher levels of hierarchy. This feedback may be either positive or negative (e.g., the relevance of the information transmitted to the inferences at higher levels). Accordingly, the system may decide whether to send this pattern higher up the levels or not, and if so whether it should it send through a different path.
  c. Checking for frequently required ISs and pick the top 'F' percentile of them.
  d. Ensuring it keeps this data ready.

In one embodiment, information used at every node may act as agents reporting on the status of a hierarchical network. These agents are referred to as Information Entities (In En). In En may provide insight about the respective inference operation, the input, and the result which collectively is called knowledge.

This knowledge may be different from the KB. For example, the above described knowledge may include the dynamic creation of insights by the system based on its inference, whereas the KB may act as a reference for inference and/or analysis operations. The latter being an input to inference while the former is a product of inference. When this knowledge is subscribed to by a consumer (e.g. administering system or another node in a different layer) it is called "Knowledge-as-a-Service (KaaS) which may serve one or more of the following purposes:
  a. When knowledge is subscribed to, it may help in identifying those In En that are relatively more active than the rest. Hence, the frequency of subscription may be tracked and the most active In En may be prioritized accordingly. This may be useful for situations where communication bandwidth is limited and not all input can be provided to all nodes at once. In those cases, the input corresponding to the "most common In En" may be sent first, thereby satisfying the majority of the requirements to the nodes. It is to be noted that In En may be state bound and static (e.g., with time, new knowledge is derived from old one). But the parent-child relationship between them may be established and used as a reference. The new knowledge entity (NeoEn) may be used in another inference in another node. This NeoEn may also report to a subscriber. In one embodiment, the subscriber need not necessarily call the respective In En or NeoEn. Rather, the subscriber may define certain conditions alone. Any InEn/NeoEn that satisfies these conditions may automatically provide information. Each InEn and NeoEn may also include metadata where a set of rules are defined which makes it eligible to be considered for respective situations. These situations may be defined by a service provider in the conditions.
  b. By reporting information, InEn/NeoEn may provide feedback on the hierarchical network. This process may aid in detection of malfunctions or errors in nodes and/or create a log registry for the activities of nodes.
  c. Time-based reporting may track trends of knowledge maturity as well as overall functioning of the hierarchical network.

The APS 304 may further include a Smart Data Runner (SDR). The SDR may choose the most relevant IS to subscribe to (e.g. for use in a given inference in a given node for a given context (time & state)). The SDR may assist an analyst to define IS to be used for each operation in a given hierarchical layer. The SDR may automate certain aspects of the tasks done by the analyst. This process may include one or more of the following:
  a. For every event to be defined, a list of data variables and/or their patterns and POP™ may be provided to the analyst by the SDR.
  b. The analyst may choose a particular set of data, patterns, and/or POP™ (e.g input) and may assign one or more weights. These weights may signify the priority of each input within a given class of inference.
  c. Inferences can be organized into various classes such as:
    i. Time-based and frequency-based;
    ii. Short-term and long-term; and/or
    iii. Single inference and multiple related inferences;
  d. Various combinations of input may be used for the given inference. In one embodiment, a comparison analysis is done and coefficients of dependencies are found.
  e. Based on a differential operator, independent relationships (i.e. each variable with the resulting variable) may also be found.
  f. These coefficients and relationships for every combination may be provided to the analyst. All combinations may then be ordered by decreasing order of probability calculated for the resulting variable. This may ensure that the best results alone are on the top and chosen, thereby considering the associated coefficients & relationships to be optimal.
  g. The analyst then may change weights or remove any variable(s) (e.g., using CES 312 or presentation layer 306). The analyst may also provide a rationale for the change (e.g. by selecting a reason from a list of them.)
  h. The SDR may perform K-means clustering on the difference between modified weights and initial weights to find the centroid and hence the optimum value of delta. It is to be noted that this may be done on 'n' events in a given class of inference. In one embodiment, this delta is specific to a given cause(s) as specified by the analyst.

i. When the next event data (e.g. training data, not an actual event) is provided, if the given causes match, then the SDR may add the optimum delta to specified weight and may provide new weights to the analyst.

j. This procedure may be repeated until delta becomes infinitesimally small (e.g. an accuracy of 95%). For example, the SDR may accurately predict the weights that would be manually entered by the analyst.

k. When higher levels of inference are defined, the variables with high weights in each class may be taken and compared with each other (i.e., interclass).

Accordingly, the SDR may help identify the most relevant information to be considered for a given inference. The SDR may be an offline system used by an analyst. Because the specified version may operate in a human supervised mode, SDR may not dynamically make decisions on choosing relevant information on its own when overall system runs online on the actual reported data.

Once the analyst designs all inferences, the respective information to be used as input may specified in the following fashion.

a. Every inference may have a space-based and/or time-based context, specified as values for certain variables called Context Variables (CV). CV could be Boolean and/or numeric and may be placed outside the transactional database.

b. Every IS may include metadata by which certain conditions are specified that relate to each possible context within the scope of overall application.

c. Whenever a context is specified, all variables that have conditions in metadata related to that context may process their conditions. If found eligible, they may be communicated to the application which then uses them for the given inference.

This process may extend the analyst-based analysis by adding time-based configuration capabilities.

In the SDR, various dependencies between IS may be specified. Accordingly, the system may use this information to find combinations within IS and their respective probabilities. These combinations may be automated and used to discover new patterns and relationships between them. This process is known as 'Relationship Discovery'. Since the SDR may operate on both live and example data it can operate in online and offline modes.

When it is operated in an online mode, it may serve as a relationship discovery tool. Similar to methodology followed in the SDR, the system may try to mimic the accuracy of the analyst in the process of defining new rules from discovered relationships.

The APS 304 may use one or more communication protocols. For example, APS 304 may outsource the statistical operations involved at various levels, such as K-means clustering, regression analysis, etc., to the SS 305. Both SS 305 and APS 304 may call the each other on demand. When the SS 305 is the service provider, the APS 304 may subscribe to statistical results. But when APS 304 is the service provider, the subscription may be probability values, data, or patterns.

The APS 304 may also communicate with the CEMS 312. The APS 304 may provide information on patterns and POP™. One purpose of APS 304 may be to provide KaaS to CEMS 312. But, the GEMS 312 may access this information as coefficients for behavior and/or clinical models. Accordingly, the pattern comparison characteristics at all levels may be transformed into relative measures. These measures form the model coefficients. They may be sent from APS 304 to GEMS 312. In return, once the cause-effect analysis is done, the result may be communicated as feedback to APS 304. This way, the APS 304 can improve its accuracy of the information it delivers the next instance.

APS 304 may also communicate the temporal information of patterns and data to the ILS 311. This communication may be used in determining the sequence of interventions during intervention planning.

The SS 305 may include statistical techniques, methods, and/or algorithms to be used by one or more of the other services, and may be implemented using some or all of the features or the type of statistical analysis of the SS 305 as described herein.

The CEMS 312 may include various mathematical models related to a patient which may be specific to one or more behaviors and/or determinants, and may be implemented using some or all of the features of the CEMS 312 as described below.

The CEMS 312 may provide insight about the dynamics of a patient's behavior and an analysis of causes for an observed behavior. Some of the features of the CEMS 312 may include dynamically updating coefficients for parameters in any given model, based on information from the APS 304, performing cause-effect analysis online, attaching a weight for each cause and infer one or more causes to be reasons for an observed behavior, providing feedback on the effectiveness of each intervention, including user experience, and/or providing insights about necessity for newer types of interventions.

CEMS 312 may be used for identifying behavior and clinical causes for events and their impact(s) on the desired outcome. An event is generally an observed abnormality in certain conditions. This can be both prolonged and discrete in nature. By prolonged, it means that the event is happening for a considerable length. Discrete events are single occurrences. The CEMS 312 may include several mathematical and logical models which essentially provide relationships among various factors of cause and effect for a given context. Then, the CEMS 313 may map them to 'actions' taken by the patient/end-user as well as those taken by associated users. Their actions directly/indirectly can affect the outcome for the end-user. Hence the Associated User (AU) and their reported data may also be included along with patient data, for these models.

Behavior models are classified into four categories as follows:

a. Outcome-based;
b. Behavior-based;
c. Determinant-based; and
d. Intervention-based.

One or more of the following rules of thumb may be applied during behavioral modeling:

One or more interventions affect determinants;
One or more determinants affect behavior; and
One or more behaviors affect outcome.

A behavior is defined to be a characteristic of an individual or a group towards certain aspects of their life such as health, social interactions, etc. These characteristics are displayed as their attitude towards such aspects. In analytical terms, a behavior can be considered similar to a habit. Hence, a behavior may be observed POP™ for a given data from a user. An example of a behavior is dietary habits.

Determinants may include causal factors for behaviors. They either cause someone to exhibit the same behavior or cause behavior change. Certain determinants are quantitative but most are qualitative. Examples include one's perception about a food, their beliefs, their confidence levels, etc.

Interventions are actions that affect determinants. Indirectly they influence behaviors and hence outcomes. System may get both primary and secondary sources of data. Primary sources may be directly reported by the end-user and AU. Secondary data may be collected from sensors such as their mobile phones, cameras, microphone, as well as those collected from general sources such as the semantic web.

These data sources may inform the system about the respective interventions. For example, to influence a determinant called forgetfulness which relates to a behavior called medication, the system sends a reminder at an appropriate time, as the intervention. Then, feedback is obtained whether the user took the medication or not. This helps the system in confirming if the intervention was effective.

The system may track a user's interactions and request feedback about their experience through assessments. The system may use this information as part of behavioral modeling to determine if the user interface and the content delivery mechanism have a significant effect on behavior change with the user. The system may use this information to optimize its user interface to make it more personalized over time to best suit the users, as well as to best suit the desired outcome.

For example, if the user provides feedback that they dislike textual display of information and also that they feel the quantity of content delivered is excessive, that feedback may be used as an input to optimize and/or choose the content and delivery method desirable by the user. In this case, it can be a simple visualization of information (instead of textual) and restricting it to 3 contents per day (e.g., instead of 10).

Every term in a given behavior model may be assigned a coefficient. Coefficient may signify the relationship it has with other terms for a given result. A simple example of a behavioral model is shown below.

$$(\text{Determinants})\beta 1 X1+\beta 2 X2+\beta 3 X3+\beta 4 X4=Y(\text{Behavior})$$

$$(\text{Interventions})\phi Z1+\phi 2 Z2+\phi 3 Z3=Xj(\text{Determinant})$$

For example, in the above liner model, $\beta 1$, $\beta 2$ and $\beta 3$ are the coefficients for interventions $\phi 1$, $\phi 2$ and $\phi 3$. For example, $\phi 1$ may be messages, $\phi 2$ may be goals, and $\phi 3$ may be learning libraries.

These interventions are mapped to a determinant Xi. Hence the influence of these interventions on an observed determinant change is found. The coefficients are used as a means to identify respective causes and their degrees of influence.

The coefficients may be constructed based on information about observed patterns from the APS 304. Event(s) information along with relevant patterns, variables, and their relationship information may be sent as part of this subscription of service. This may then be used in a well-defined Behavioral Mathematics framework to exactly identify causes for the observed effect.

Models in CEMS 312 also may accommodate data obtained directly from the end-user, such as assessments, surveys, etc. This enables users to share their views on interventions, their effectiveness, possible causes, etc. The system's understanding of the same aspects is obtained by way of analysis and service by the APS 304.

Both system-perceived and end user-perceived measures of behavioral factors may be used in a process called Perception Scoring (PS). In this process, hybrid scores may be designed to accommodate both above mentioned aspects of behavioral factors. Belief is the measure of confidence the system has, when communicating or inferring on information. Initially higher beliefs may be set for user-perceived measures.

But over time, as the system finds increasing patterns as well as obtains feedback in APS 304, the GEMS 312 may evaluate the effectiveness of intervention(s). If the system triggers an intervention based on user-perceived measures and it doesn't have significant effect on the behavior change, the system may then start reducing its belief for user-perceived measures and instead will increase its belief for system-perceived ones. In other words, the system starts believing less in the user and starts believing more in itself. Eventually this reaches a stage where system can understand end-users and their behavioral health better than end-users themselves. When perception scoring is done for each intervention, it may result in a score called Intervention Effectiveness Score (IES).

Perception scoring may be done for both end-users as well as AU. Such scores may be included as part of behavior models during cause-effect analysis.

Causes may be mapped with interventions, determinants, and behavior respectively in order of the relevance. Mapping causes with interventions helps in back-tracking the respective AU for that cause. In simple terms, it may help in identifying whose actions have had a pronounced effect on the end-user's outcome, by how much and using which intervention. This is very useful in identifying AUs who are very effective with specific interventions as welt as during certain event context. Accordingly, they may be provided a score called Associated User Influence Score (AU IS). This encompasses information for a given end-user, considering all interventions and possible contexts relevant to the AU.

The CEMS 312 may also use one or more communication protocols. For example, certain behavior models may require statistical operations such as regression analysis, clustering, etc. Those tasks may be outsourced to the SS 305 on demand. The statistical result may then be communicated back to GEMS 312 by suitable conversion of the results in a CEMS-readable format. The CEMS 312 may also provide sets of causes, their coefficients, IES, and/or AUIS to the ILS 311.

The ILS 311 may construct one or plans including one or more interventions based on analysis performed by the GEMS 312, and may be implemented using some or all of the features of the ILS 311 as described below.

Some of the features of the ILS 311 may include evaluating eligibility of an intervention for a given scenario, evaluating eligibility of two or more interventions based on combinatorial effect, prioritizing interventions to be applied, based on occurrence of patterns (from APS 304), and/or submitting an intervention plan to DS 302 in a format readily usable for execution.

In one embodiment, the ILS 311 may suggest to the AU a few tasks while the system directly implements other tasks to the end user. Hence, the end user gets the impact of these tasks, both from AUs as well as from the system. The AU may provide information about the progress towards desired outcome. This desired outcome may be twofold in nature—one that is global and other that is local. Global refers to holistic outcomes that cannot be achieved directly. These outcomes need few other outcomes to be achieved as a prerequisite. Local refers to those outcomes that are independent and can be achieved directly. Hence, a global outcome may require two or more local outcomes to be achieved. An example is to have a good quality of life, which is a global outcome in this case, one is required to have stable health, stable personal finances, etc., which are local outcomes.

This service may rely on the cause-effect analysis by CEMS, for its planning operations. A plan consists of interventions and a respective implementation schedule. Every plan may have several versions based on the users involved in it. For example, the system may have a separate version for the physician as compared to a patient. They will in turn do the task and report back to the system. This can be done either directly or the system may indirectly find it based on whether a desired outcome with the end user was observed or not.

The methodology employed by SDR and ILS 311 may be predefined by an analyst. For every cause, which can be an intervention(s), determinant(s), behavior(s) or combinations of the same, the analyst may specify one or more remedial actions using CEMS 312 or presentation layer 306. This may be specified from the causal perspective and not the contextual perspective.

This approach uses the idea of situation-aware metadata description framework meaning that context specific information for all possible contexts specified in the meta data during system design. This process may be done for every cause, thereby specifying what remedial actions are more appropriate for it and for what context.

Accordingly, a set of remedial actions may be confirmed by considering IES as well. AUIS may be used in determining which users should participate in the intervention plan and how. For example, if a physician had a high AUIS score for improving confidence of a patient, the intervention plan may consider that fact and include one of the interventions to be motivational interviewing of the patient by that physician, provided the cause-effect analysis confirms it with a closely associated cause.

The ILS 311 may communicate with the DS 302 for status update on the current set of interventions being sent to all users. Accordingly, the ILS may optimize its plan to ensure that it reflects a smooth transition between plans (current versus new) and hence interventions to the end user. The rules for such optimizations may be manually specified by the analyst during the design.

The DS 302 may be responsible for executing the plan provided by the ILS 311, and may be implemented using some or all of the features of the DS 302 as described below. Some of the features of the DS 302 may include selecting appropriate presentation mode (e.g. web or mobile) as well as device (e.g. phone or tablet) based on the intervention specified, mapping rules to each intervention based on plan from ILS 311, operating both proactively (based on predefined plan) and reactively (feedback-based inference engine), obtaining feedback about the end-user from system usage and self-reporting, facilitating data to the APS 304 and hence made the overall end-to-end CDSS a reflexive feedback system, and/or calling the APS 304 on-demand. In the use case, the patient may be presented with articles related to the consumption of carbohydrates, given one or more carbohydrate-counting goals, and/or receive one or more notifications to perform a task, such as instructions to pick up medication or exercise.

The ILS 311 may send a new plan to DS 302 based on subscription by DS 302. This may be initiated by DS 302 when it nears the completion of the current plan. The DS 302 also has the flexibility of a 'push' of plans by ILS 311. This may be done when there is a need for change of plans significantly earlier than the end of current one. The new plan may be entirely different from the current one or it may be additional tasks in the current plan. This may be confirmed based on synchronization between ILS 311 and DS 302 during creation of the new plan.

The reason for using a plan is explained as follows. The DS 302 may be responsible for delivering appropriate tasks to all users by suitable presentation channels. In the case of a weak communication signal or a loss of network connectivity, the plans may still be executed by users due to criticality to end-users health. Accordingly, the plans may be sent to the DS 302 to complete the plan and accomplish required outcomes even in such scenarios.

On the other hand DS 302 can take advantage of a strong network coverage and higher bandwidth to customize the plan to deliver richer and more dynamic content, quicker analysis and superior real-time user experience.

The DS 302 may transform a plan into versions based on the presentation channel (web, mobile, standalone, executable program, etc.) and their capabilities. The DS 302 may employ an inference engine 307 which provides real-time support to users based on the specified plan. Inference engine 307 may be device resident and may obtain user-reported as well as device-reported data. It then facilitates this data to various services through the DS 302. Every task in a plan may be optimized to be compatible and used in an inference engine. This engine may make certain decisions based on predefined rules. Each plan may reflect changes to these rules to accommodate the revised outcome to be achieved. The rules may be mapped to content. Each piece of content may be delivered to the user by a presentation channel.

Various presentation channels are:
a. Standalone devices (computers)
b. Portable devices (mobile phones, handheld devices, intelligent systems in automobiles—cars, flights etc.)

Various presentation modes are:
a. Web portal-based
b. Application-based
   i. Standalone executable application
   ii. Server-based application There may be a communication component within every presentation channel that accepts its version of the plan through a secured communication protocol. There may also be an execution component within every presentation layer that will take care of starting the new plan at a calculated period before the completion of the current plan. This ensures that the transition between plans is smooth enough for the users to not experience a drastic change in interventions. Also, the execution component may also suppress certain flows of delivering content in the inference engine based on the new plan. This ensures that the users are not sent contents from two plans which may look confusing. Considering the context, either the new plan or the current plan may be preferred over the other. This component also may manage between both plans simultaneously, if necessary.

Every presentation channel may be associated with a presentation device. The capabilities and various sensory data input options of the device may be used by inference engine. The device-specific version of the plan is meant to address this issue. In certain cases, such as mobile phones, handheld devices, etc., where camera and microphone is available, a specific pattern recognition engine, called the Sensory Pattern Recognition Engine (SPRE), is used. The purpose of this engine is to take specific samples of pictorial, video and auditory data, using camera and microphone, and then compare it with predefined categories of emotions. Hence, it may perform a pattern classification operation. The engine may be pre-trained with example data in these formats for those respective categories. The pattern recognition mechanism may be similar to the one performed by APS 304. But in this engine, the focus may be on only sensory inputs and basic classification. Thus, it may not have any hierarchical layers of computation making it much simpler and more specific. After classification, it may compare the classification between the three sensory data sources and confirm the emotional state of the end user using suitable algorithms. This feature becomes a valuable source of information that may be used by different services for making psychological and behavioral inferences.

Accordingly, the DS 302 may send a variety of data and information to APS 304 and other services, as feedback, for these services to understand about the users. This understanding may affect their next set of plans which in turn becomes an infinite cyclic system where system affects the users while getting affected by them at the same time. Such a system is called a reflexive-feedback enabled system. The system may user both positive and negative reflexive-feedback, though the negative feedback aspect may predominantly be used for identifying gaps that the system needs to address.

Though DS 302 can subscribe to new plans through the ILS 311, it is free to communicate to other services by bypassing ILS 311. The DS 302 can subscribe to the APS 304 on demand and request for information such as patterns, their correlations, etc. which can be directly reported to users without requiring any analysis through CEMS 312. The APS 304 may provide the requested data and the DS 302 may take care of suitable reporting version based on the users and presentation channel.

The CAS 303 may provide information, such as one or more newly identified patterns, to an analyst (e.g., clinical analyst or doctor). In the use case, the doctor may be presented with one or more notifications to address the relationship between carbohydrates and the medication that the patient is taking.

The embodiments described herein, and in the attached documentation, are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A computer-implemented method for dynamically revising a patient care plan comprising:
    electronically receiving, by at least one processor, patient feedback relating to a patient care plan, wherein the patient feedback includes data entered into the at least one processor by the patient;
    decoding, using the at least one processor, patient specific data and learning one or more patterns that cause an event based on the patient specific data and one or more pattern recognition algorithms;
    determining one or more patient beneficial actions based on the learned patterns; and
    automatically preparing and presenting a revised patient care plan based on the patient specific data, the identified one or more patient beneficial actions, and the patient feedback.

2. The computer-implemented method of claim 1, wherein the patient specific data comprises data received from a patient body sample sensor.

3. The computer-implemented method of claim 1, wherein the patient specific data is a blood glucose level.

4. The computer-implemented method of claim 1, wherein the patient specific data comprises patient interaction data.

5. The computer-implemented method of claim 1, wherein the revised patient care plan is presented to a user on multiple electronic devices.

6. The computer-implemented method of claim 1, wherein the revised patient care plan comprises electronic content.

7. The computer-implemented method of claim 1, further comprising determining the speed of the patient's electronic device and presenting the revised patient care plan based on the speed of the patient's electronic device.

8. The computer-implemented method of claim 7, wherein electronic data type presented in the revised patient care plan is determined based on a processor speed of the electronic device and a speed of an electronic network to which the electronic device connects.

9. The computer-implemented method of claim 1, wherein the patient specific data is received from a patient's electronic device and comprises patient environmental data.

10. The computer-implemented method of claim 9, wherein the patient environmental data is received from optical and audio components of the electronic device.

11. A computer-implemented method for dynamically revising a patient care plan comprising:
    electronically receiving patient feedback, by at least one processor, relating to the patient care plan, wherein the patient feedback includes data entered into the at least one processor by the patient;
    decoding, using the at least one processor, patient specific data and learning one or more patterns that cause an event based on the patient specific data;
    transmitting an alert related to a non-beneficial patient action;
    determining one or more patient beneficial actions based on the learned patterns; and;
    automatically preparing a revised patient care plan based on the patient specific data, the identified one or more patient beneficial actions, and the patient feedback.

12. The computer-implemented method of claim 11, wherein the patient specific data comprises data received from a patient body sample sensor.

13. The computer-implemented method of claim 11, wherein the patient specific data is a blood glucose level.

14. The computer-implemented method of claim 11, wherein the patient specific data comprises patient interaction data.

15. The computer-implemented method of claim 11, wherein the revised patient care plan is presented to a user on multiple electronic devices.

16. The computer-implemented method of claim 11, wherein the revised patient care plan comprises electronic content.

17. The computer-implemented method of claim 11, further comprising determining the speed of the patient's electronic device and presenting the revised patient care plan based on the speed of the patient's electronic device.

18. The computer-implemented method of claim 11, wherein electronic data type presented in the revised patient care is determined based on a processor speed of the electronic device and a speed of an electronic network to which the electronic device connects.

19. The computer-implemented method of claim 11, wherein the patient specific data is received from a patient's electronic device and comprises patient environmental data.

20. The computer-implemented method of claim 11, wherein the patient environmental data is received from optical and audio components of the electronic device.

21. An information processing device for revising a patient care plan, the device comprising:
    a processor for processing a set of instructions; and
    a computer-readable storage medium for storing the set of instructions, wherein the instructions, when executed by the processor, perform a method comprising:

electronically receiving patient, by at least one processor, feedback relating to the patient care plan, wherein the patient feedback includes data entered into the at least one processor by the patient;

decoding, using the at least one processor, patient specific data and learning one or more patterns that cause an event based on the patient specific data and one or more pattern recognition algorithms;

determining one or more patient beneficial actions based on the learned patterns; and automatically preparing and presenting a revised patient care plan based on the patient specific data, the identified one or more patient beneficial actions, and the patient feedback.

22. The information processing device of claim 21, wherein the patient specific data comprises data received from a patient body sample sensor.

23. The information processing device of claim 21, wherein the patient specific data is a blood glucose level.

24. The information processing device of claim 21, wherein the patient specific data comprises patient interaction data.

25. The information processing device of claim 21, wherein the revised patient care plan is presented to a user on multiple electronic devices.

26. The information processing device of claim 21, wherein the revised patient care plan comprises electronic content.

27. A non-transitory computer-readable medium storing a set of instructions that, when executed by a processor, perform a method of providing a treatment recommendation, the method comprising:

electronically receiving, by at least one processor, patient feedback relating to a patient care plan, wherein the patient feedback includes data entered into the at least one processor by the patient;

decoding, using the at least one processor, patient specific data and learning one or more patterns that cause an event based on the patient specific data;

transmitting an alert related to a non-beneficial patient action;

determining one or more patient beneficial actions based on the learned patterns; and;

automatically preparing a revised patient care plan based on the patient specific data, the identified one or more patient beneficial actions, and the patient feedback.

28. The computer-readable medium of claim 27, wherein the patient specific data is received from a patient's electronic device and comprises patient environmental data.

29. The computer-readable medium of claim 27, wherein the patient specific data comprises data received from a patient body sample sensor.

30. The computer-readable medium of claim 27, wherein the patient specific data is a blood glucose level.

* * * * *